United States Patent [19]
Webb

[11] Patent Number: 6,041,785
[45] Date of Patent: Mar. 28, 2000

[54] PUNCTUM PLUG

[75] Inventor: Nicholas J. Webb, Wrightwood, Calif.

[73] Assignee: Eaglevision, Inc., Memphis, Tenn.

[21] Appl. No.: 09/188,011

[22] Filed: Nov. 6, 1998

Related U.S. Application Data

[63] Continuation-in-part of application No. 08/826,216, Mar. 27, 1997, which is a continuation-in-part of application No. 09/095,194, Jun. 10, 1998.

[51] Int. Cl.[7] ............................................. A61B 17/00
[52] U.S. Cl. ................................... 128/887; 604/4
[58] Field of Search ...................... 604/4, 8, 9, 10, 604/54; 623/4; 128/887

[56] References Cited

U.S. PATENT DOCUMENTS

| | | | |
|---|---|---|---|
| 3,949,750 | 4/1976 | Freeman | 128/260 |
| 4,915,684 | 4/1990 | MacKeen | 604/8 |
| 5,723,005 | 3/1998 | Herrick | 604/8 |

*Primary Examiner*—Michael A. Brown
*Attorney, Agent, or Firm*—David P. Gordon; David S. Jacobson; Thomas A. Gallagher

[57] ABSTRACT

A punctum plug includes a proximal head, a distal body, and a shaft between the head and the body. The shaft of the plug is provided with one or more foldable portions, thereby permitting the length of the shaft to vary depending upon the degree to which the folds are folded or unfolded. In addition, the folds permit the wall of the shaft to easily bend, permitting the head and body of the plug to lie along different axes. As a result, the plug is shaped to accommodate both relatively long and short vertical puncta and the body of the plug may be angled relative to the head to accommodate a variety of anatomical structures.

27 Claims, 10 Drawing Sheets

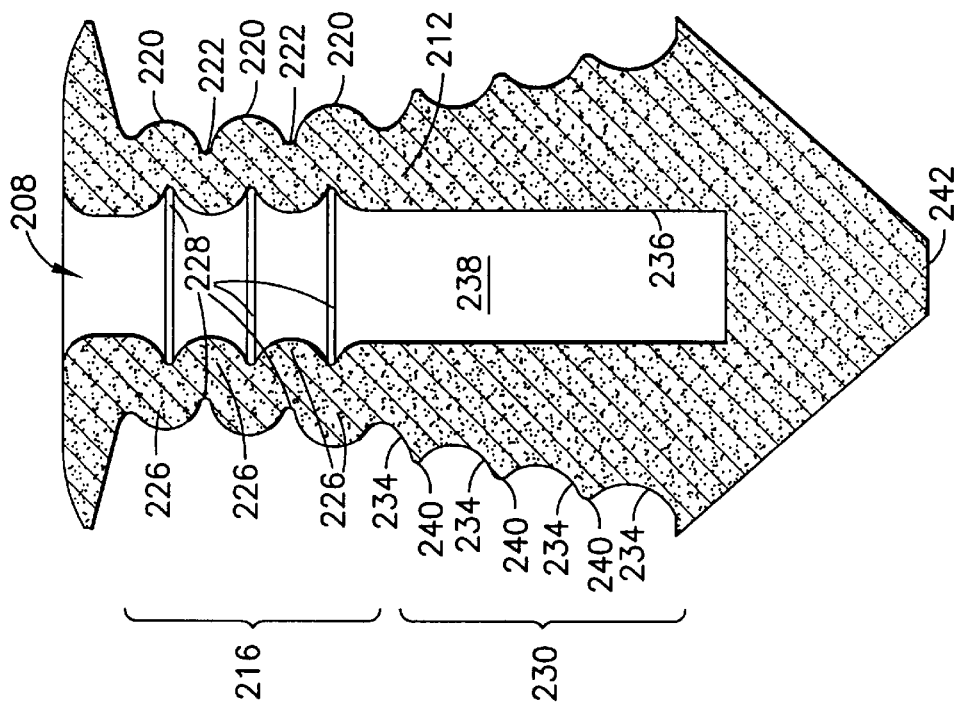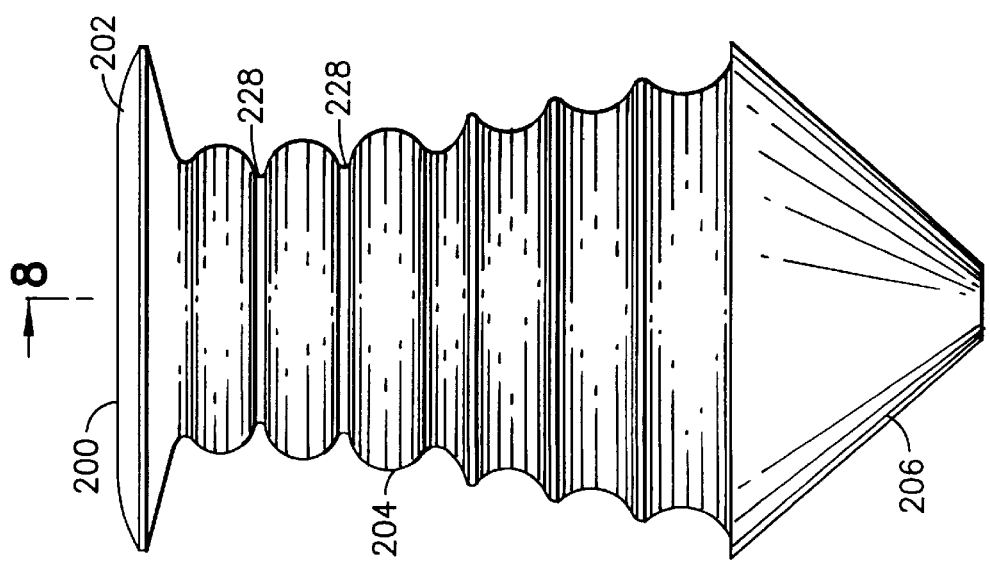

PUNCTUM PLUG

This application is a continuation-in-part of U.S. applications Ser. No. 08/826,216, filed Mar. 27, 1997, and Ser. No. 09/095,194, filed Jun. 10, 1998, both of which are hereby incorporated by reference herein in their entireties.

BACKGROUND OF THE INVENTION

1. Field of the Invention

This invention relates broadly to medical canalicular inserts. More particularly, this invention relates to plugs which are placed into the punctal opening of the lacrimal duct to prevent lacrimal fluid from flowing through the lacrimal duct.

2. State of the Art

A variety of eye problems are related to an insufficient volume of tears on the surface of the eyes. The most common is keratoconjunctivitis sicca, also known as dry eyes. Contact lens problems are also often provoked by a lack of tear volume. A common cause for the insufficient tear volume is the drainage of tear fluid through the punctal opening of the nasal lacrimal duct and into the nasal passage, thereby removing the fluid from where it is needed at the eye surface. Furthermore, drainage of tear fluid through the nasal lacrimal duct into the nasal passage is believed to be the cause or associated with several additional problems such as post nasal drip, sinusitis, allergies, headaches, and snoring.

A number of methods for closing the punctal opening have been used to prevent drainage of tears through the nasal lacrimal duct, including suturing, laser sealing, and plugging. Plugging with a punctum plug is the least severe solution, is relatively inexpensive, and is being performed with increasing frequency.

Referring to prior art FIG. 1, a punctum plug 10 typically is an elongate member having a proximal head 12, a large distal body 14 for occluding the lacrimal duct 16, and a narrow rigid shaft 18 therebetween. The plug is usually provided with a proximal axial bore 20 for receiving an insertion tool. In the punctum plug insertion procedure, an insertion tool is positioned into the plug, the body of the plug is directed at the punctal opening 22 of the lacrimal duct 16, and force is applied to the insertion tool to move the body of the plug through the punctal opening and into the vertical puncta 24 and lacrimal duct 16. Once the plug is in the vertical puncta and lacrimal duct, the insertion tool is removed. The plug is fully inserted when the head seats against the tissue at the punctal opening and the body seats within the lacrimal duct so as to block the passage of tear fluid and thereby retain tear fluid at the surface of the eye.

It has been found that some prior art punctum plugs fail to properly seat against the tissue at the punctal opening, which may result in discomfort or inadvertent dislodging. This is believed to occur because some persons have relatively short vertical puncta. As a result, the body of the plug, rather than resting within the vertical puncta, is forced against the duct tissue 26 where the vertical puncta meets the lacrimal duct. This urges the plug upwards and can cause the plug to be unintentionally dislodged. In addition, the duct tissue 26 may become irritated therefrom.

Another problem of the prior art plugs is that pressure buildup within the lacrimal duct, for example, as caused by sneezing, can cause the relatively stiff plug to be moved up and out of the punctum.

SUMMARY OF THE INVENTION

It is therefore an object of the invention to provide a punctum plug which fully blocks tears from flowing into the punctal opening of the nasal lacrimal duct.

It is another object of the invention to provide a punctum plug which is not easily unintentionally removed from the puncta.

It is also an object of the invention to provide a punctum plug which adjusts to the length of the vertical puncta of the individual into which the plug is inserted.

It is a further object of the invention to provide a punctum plug in which the head of the plug may lie along a different axis than the body of the plug.

In accord with these objects which will be discussed in detail below, a punctum plug is provided generally having a proximal head, a distal body, and a flexible shaft between the head and the body. The shaft is preferably tapered in the direction from the body to the head. The plug preferably includes a proximal bore to assist in inserting the plug at the implant site. The head is preferably provided with a lower portion having a frustoconical shape which, in situ, reduces the external profile of the head (i.e., the height of the portion of the head which rises above the punctal opening), without sacrificing the thickness of the head. The body preferably includes a ridge at the juncture of the shaft and the body.

According to a first preferred embodiment of the invention, at least a first (and preferably upper) portion of the wall of the shaft of the plug is preferably comprised of an undulating wall. The exterior surface of the first portion of the wall has a plurality of circumferential convexly curving portions defining indentations therebetween which act as folds. The interior surface of the first portion of the wall has a plurality of inwardly directed convexly curving portion which define additional indentations which act as additional folds in the wall. The folds of the exterior surface are aligned with the convexly curving portions of the interior surface and vice versa. The folds permit the length of the shaft to vary depending upon the degree to which the folds are folded or unfolded. A second (and preferably lower) portion of the wall of the shaft preferably includes an exterior surface provided with additional convexly curving portions defining additional indentations and an interior surface defining a substantially cylindrical portion of the bore. Each of the convex curves on the exterior surface preferably includes a lateral "apex".

According to a second embodiment, a first (and preferably upper) portion of the shaft includes an undulating wall in which both the exterior and interior surface of the wall include circumferential convexly curving portions which define inner and outer folds, as in the first embodiment. In addition, a second (and preferably lower) portion of the wall includes an exterior surface defining a plurality of circumferential concave curves, with apexes being defined therebetween, while the interior surface preferably defines a substantially cylindrical bore.

Other embodiments are also provided. According to a third embodiment, the wall of the shaft of the plug is provided with angular accordion-like folds. According to a fourth embodiment, the entire wall of the shaft is provided with folds; i.e., the interior surface defines a bore which has folds substantially along its entire length. According to a fifth embodiment, one or more helical, rather than circumferential, folds are provided. According to a sixth embodiment, the shaft of the plug is substantially non-tapered. According to a seventh embodiment of the invention, the plug is provided with a collapsible skirt which, upon collapse toward the shaft, operates similarly to the tapered shaft to enhance the fit and security of the plug within the punctum.

The undulating, fold-provided wall of the shaft of the plug is adapted to accommodate both relatively long and short vertical puncta. In addition, the folds provide a highly flexible shaft which permits the head and body of the plug to lie along different axes, particularly useful in persons having short vertical puncta. That is, the body of the plug may be angled relative to the head to accommodate a variety of anatomical structures. In addition, the folds in the shaft of the plug are adapted to absorb negative pressure, e.g., from sneezing. Moreover, the apexes of the exterior curves and the ridge between the body and the shaft provide traction against the walls of the puncta, reducing the likelihood of inadvertent dislodging of the plug, while offering improved comfort. Also, the low profile head rests low in the punctal opening substantially preventing irritation of the eye.

Additional objects and advantages of the invention will become apparent to those skilled in the art upon reference to the detailed description taken in conjunction with the provided figures.

BRIEF DESCRIPTION OF THE DRAWINGS

Prior art

FIG. 7 is a side elevation view of a punctum plug according to the second embodiment of the invention;

FIG. 8 is a section view across line 8—8 in FIG. 7;

DETAILED DESCRIPTION OF THE PREFERRED EMBODIMENTS

Figure 1:
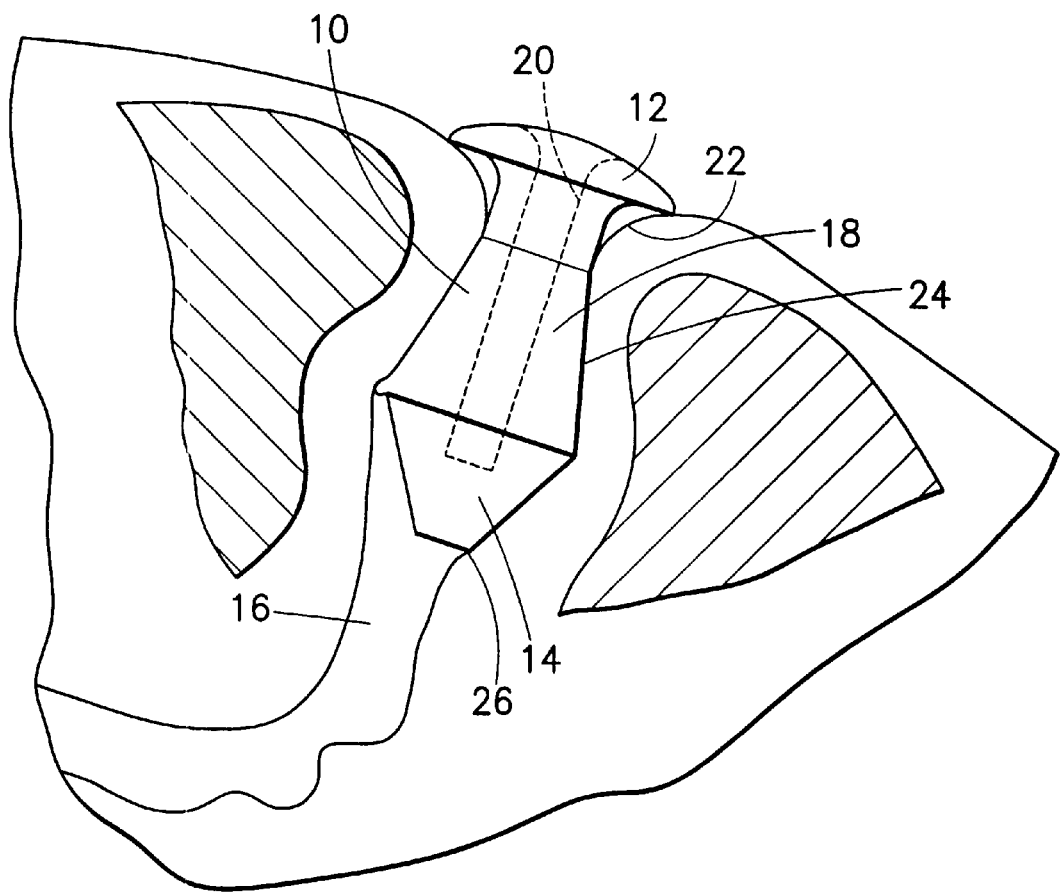
FIG. 1 is a side elevation view of an implanted prior art punctum plug.
Figure 3:
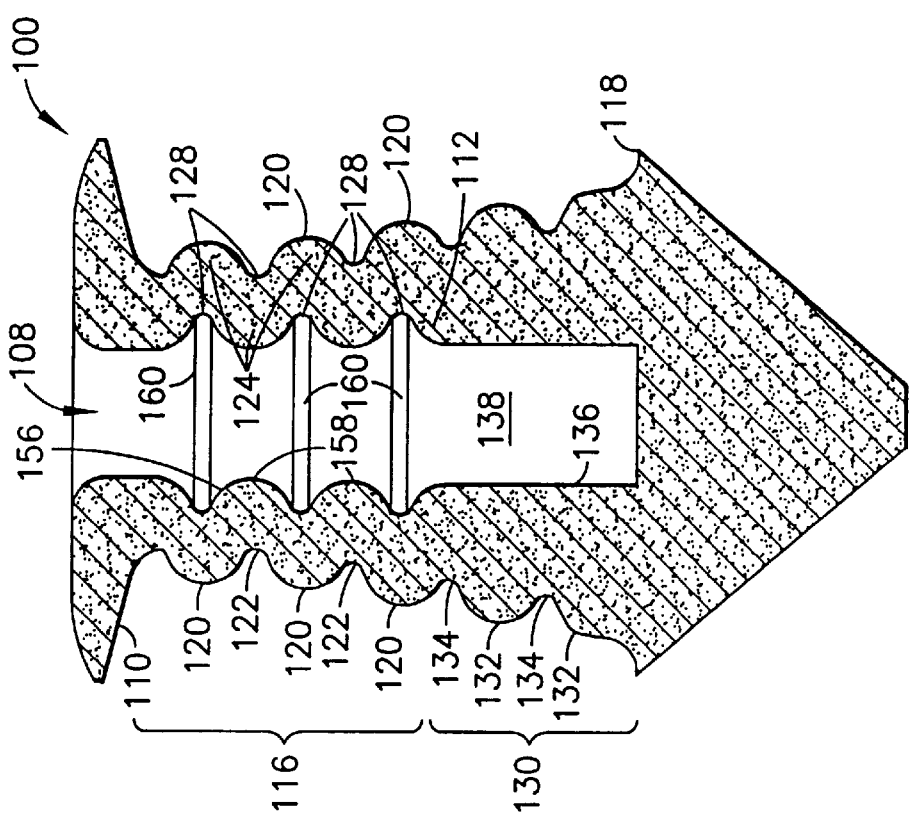
FIG. 3 is a section view across line 3—3 in FIG. 2.
Figure 2:
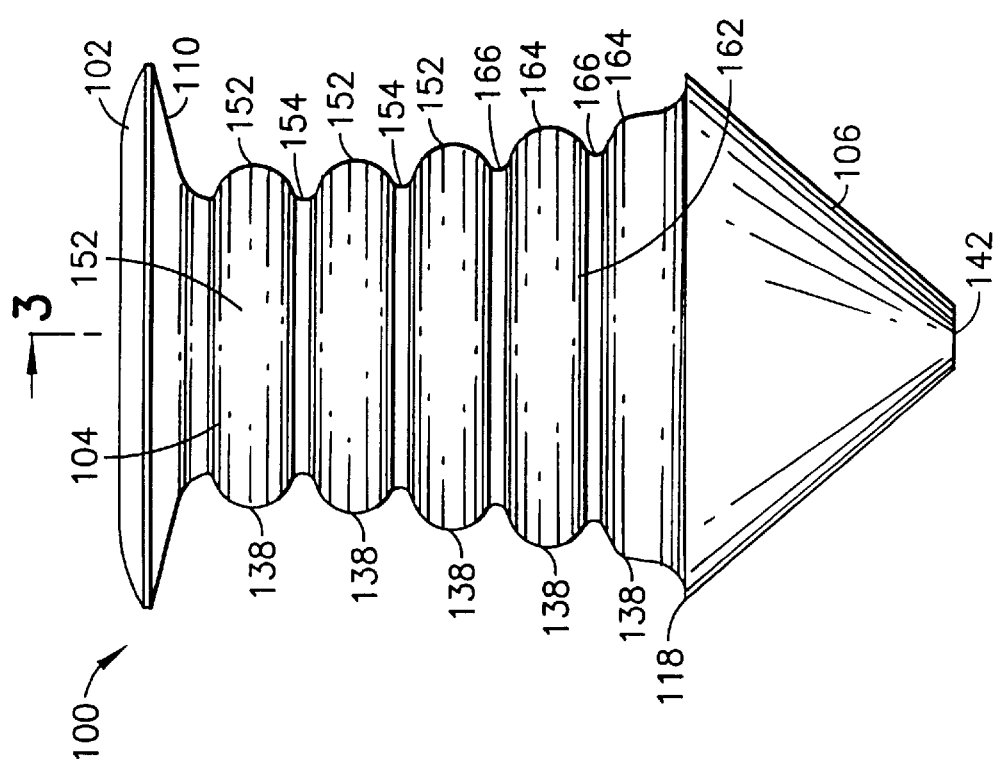
FIG. 2 is a side elevation view of a punctum plug according to a first embodiment of the invention.

Turning now to FIGS. 2 and 3, a first and presently preferred embodiment of a punctum plug 100 according to the invention is shown. The punctum plug 100 generally includes a head 102, a shaft 104 and a body 106. An axial bore 108 is provided through the head 102 and shaft 104, and may extend into the body 106 (as shown in FIG. 8 with respect to the second embodiment of the invention). Preferably, the plug is made from silicone or another soft, low durometer material, by liquid injection molding, cast molding, or transfer molding.

Figure 6:
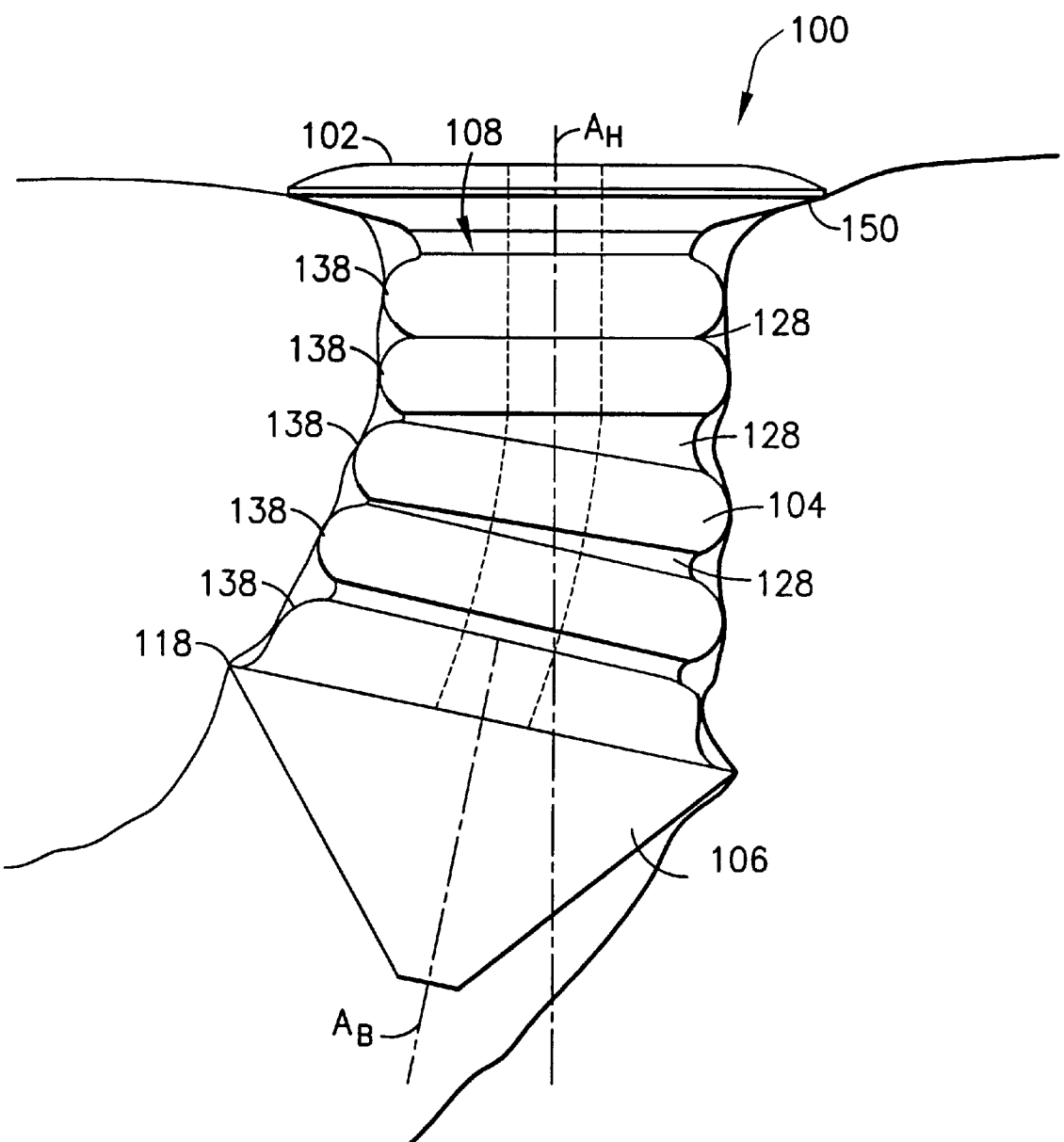
FIG. 6 is a side elevation view of an implanted punctum plug according to the first embodiment of the invention.

The head 102 of the plug is preferably as described in previously incorporated U.S. application Ser. No. 09/095,194, although it is within the scope of this invention to use any other head design. Briefly, with respect to the preferred head 102, the head is preferably provided with a lower portion 110 having a frustoconical shape which, in situ, reduces the external profile of the head (i.e., the height of the portion of the head which rises above the punctal opening, as shown in FIG. 6), without sacrificing the thickness of the head.

The body 106 is preferably frustoconical in shape, and the body 106 preferably defines a ridge 118 at the juncture of the shaft 104 and the body 104. The ridge 118 functions to provide occlusal capability to the plug and also traction to the walls of the punctum to thereby assist in maintaining the plug within the punctum. The tip 142 of the body is preferably truncated, yet has a distal diameter preferably smaller than the punctal opening.

The diameter of the shaft 104 is preferably tapered in the direction of the body 102 to the head 106. The shaft 104 includes a wall 112 surrounding the axial bore 108. According to a first preferred embodiment of the invention, a first (and preferably upper) portion 116 of the wall 112 of the shaft 104 is provided with substantially circumferential alternating convex rings 120 and concave rings 122, and the wall is preferably of a substantially constant thickness. Stated another way, referring to FIG. 2, the exterior surface 150 of the first portion 116 of the wall 112 has a plurality of circumferential convexly curving portions 152 defining indentations 154 therebetween which act as folds. Referring to FIG. 3, the interior surface 156 of the first portion 116 of the wall 112 has a plurality of inwardly directed convexly curving portions 158 which define additional indentations 160 which act as additional folds in the wall. The indentations 154 of the exterior surface 152 are aligned with the convexly curving portions 158 of the interior surface 156 and vice versa. Referring to FIGS. 2 through 5, the folds 128 provide the wall 112 with preferably smooth and wave-like undulations 124, which permit the length of the shaft 104 to be compressed (FIG. 4) and to be expanded (FIG. 5) depending upon the degree to which the folds are folded or unfolded. The first portion 116 of the shaft 104 is thereby adapted to accommodate both relatively long and short vertical puncta.

Turning back to FIGS. 2 and 3, preferably a second (and preferably lower) portion 130 of the wall 112 of the shaft 104 includes exterior alternating convex rings 132 and concave rings 134. Stated another way, the wall 112 of the shaft preferably includes an exterior surface 162 provided with convexly curving portions 164 which define indentations 166. An interior surface 136 defines a substantially cylindrical portion 138 of the bore 108. In addition, the wall 112 at the second portion 130 is preferably of a nonconstant thickness (and changing in thickness at a nonconstant rate along a length of the wall), generally tapering in thickness in the direction of the body 106 to the head 102. The shaft 104 of the plug is preferably adapted to bend, though not lengthen or shorten in length, at the indentations 166. Each of the convex and concave rings 120, 122, 132, 134 includes a lateral "apex" 138.

Plugs may be provided in several sizes to provide satisfactory insertion into puncta of varying dimensions and to thereby occlude the nasal lacrimal duct. By way of example, and not by way of any limitation, the following dimensions are provided for one size of the first embodiment of the punctum plug. The plug 100 has a length of approximately one sixteenth inch to one half inch from head 102 to tip 142 of the body 106 when in a compressed state and a length of approximately five sixty-fourths inch to one-inch when in an expanded state. The head has a diameter of approximately 0.040 inches. The shaft has a diameter ranging from approximately 0.020 to 0.035 inches.

Referring to FIG. 6, the plug 100 is inserted as follows into the punctum to block the flow of tears through the nasal lacrimal duct. An insertion tool (not shown) is inserted into the bore 108 of the plug to provide with plug with rigidity and manipulability. The body 106 of the plug is brought to the punctal opening 150. The insertion tool is manipulated to slowly force the plug into the punctal opening. The plug is inserted in this manner until the head 102 seats substantially flush around the punctal opening 150. Once the plug is inserted, the insertion tool is removed thereby allowing the shaft 104 of the plug to flex.

Figure 5:
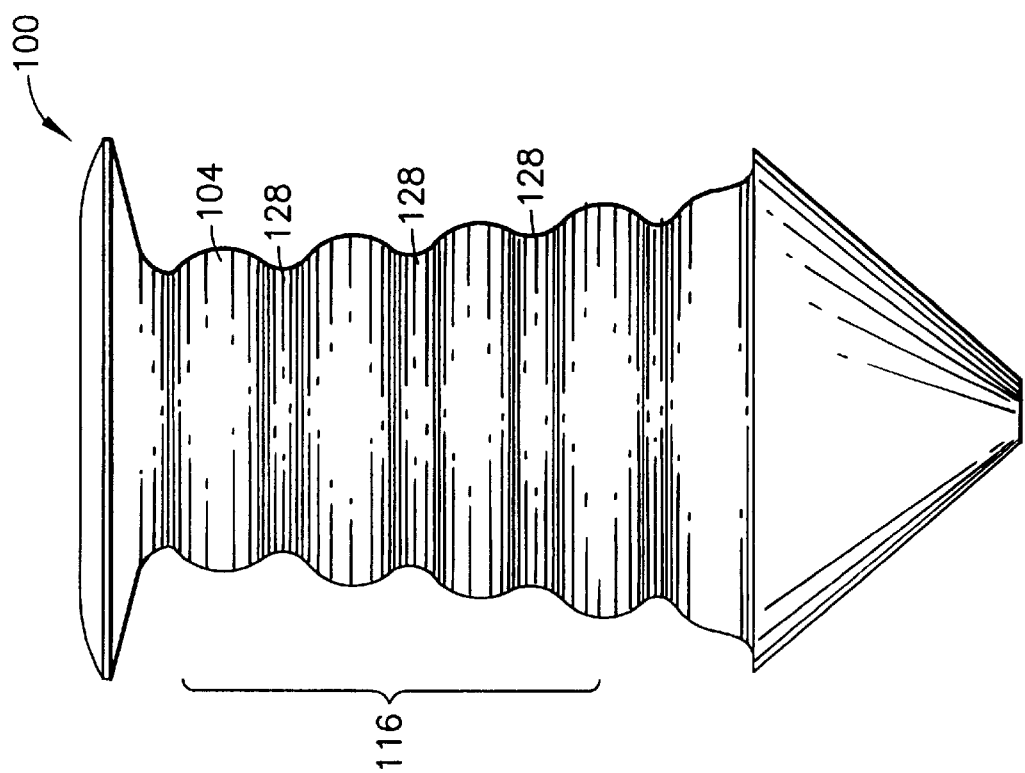
FIG. 5 is a side view of the first embodiment of a punctum plug according to the first invention shown in an axially elongated configuration.
Figure 4:
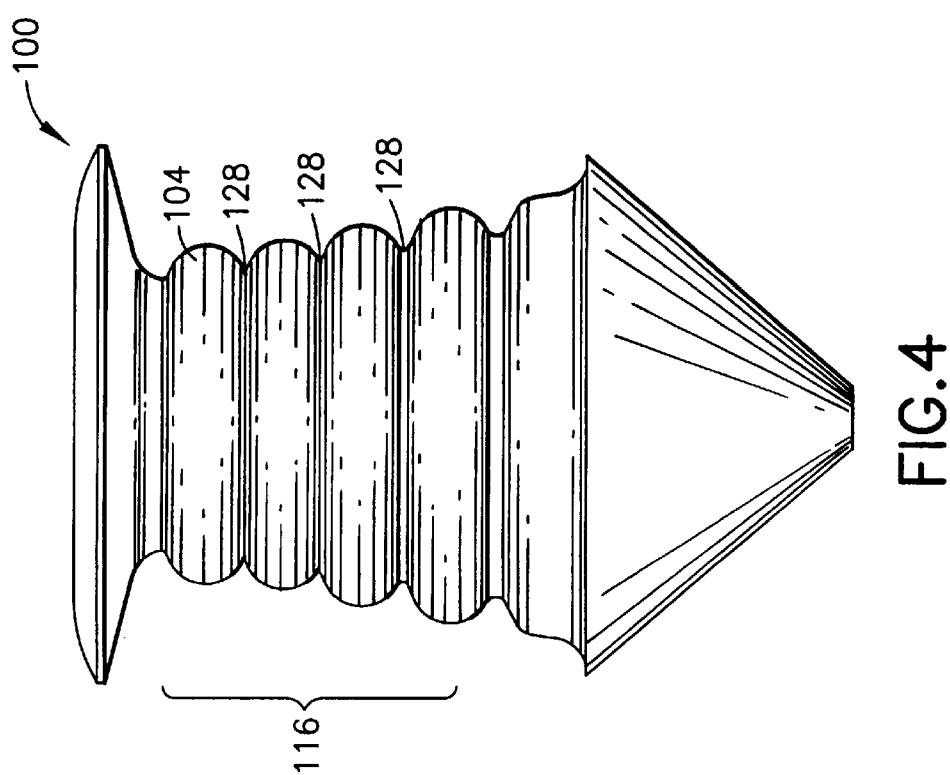
FIG. 4 is a side view of the first embodiment of a punctum plug according to the first invention shown in an axially compacted configuration.

The plug 100 is able to accommodate and be securely seated in a variety of anatomically configured puncta. The folds 128 permit the shaft to shorten and elongate as needed (as shown in FIGS. 4 and 5). Moreover, the folds 128 provide the shaft with high flexibility, permitting the body 106 to lie along a body axis $A_B$ which is angled relative to the axis $A_H$ extending axially through the head 102 of the plug. That is, the body 106 of the plug may be angled relative to the head 102 to flex the plug within the vertical punctum. The ability of the plug shaft to vary in length and to flex are particularly useful with respect to people having short vertical puncta. In addition, the soft apexes 138 of the curves along the exterior surface and the ridge 118 between the body and the shaft provide traction against the wall of the puncta, reducing the likelihood of inadvertent dislodging of the plug, while offering improved comfort. Furthermore, the folds 128 in the shaft 104 of the plug are adapted to absorb negative pressure, e.g., from sneezing. When the lacrimal duct is provided with a rapid increase in pressure, the shaft 104 of the plug compresses and absorbs the pressure like a spring to dissipate the pressure. Also, the low profile head rests low in the punctal opening, thereby substantially reducing eye irritation.

Turning now to FIGS. 7 and 8, a second embodiment of a punctum plug 200, substantially similar to the first embodiment (with like parts having numbers incremented by 100), is shown. The plug 200 includes a head 202 and a body 206, preferably substantially as described above with respect to the first embodiment, and a shaft 204 therebetween. The shaft 204 of the plug includes a first (and preferably upper) portion 216 also substantially similar to the first portion 116 of the first embodiment; i.e., such that alternating convex and concave rings 220, 222 form a plurality of folds 228 in the wall 212 which provide the wall with preferably smooth wave-like undulations 226. In accord with the second embodiment of the invention, a second (and preferably lower) portion 230 of the wall 212 includes exterior substantially circumferential concave rings 234, and a lateral "apex" 240 between adjacent concave rings 234. The interior surface 236 of the second portion 230 of the wall 212 preferably defines a substantially cylindrical portion 238 of the bore 208. The plug diameter generally increases as it extends toward the tip 242, and the wall thickness of the second portion 230 also increases as it extends toward the tip.

The second embodiment of the punctum plug provides similar advantages as the first embodiment. In addition, the "apexes" 240 along the lower portion 230 of the wall 212 provide significant traction and gripping for stability and fixation within the punctum.

Figure 9:
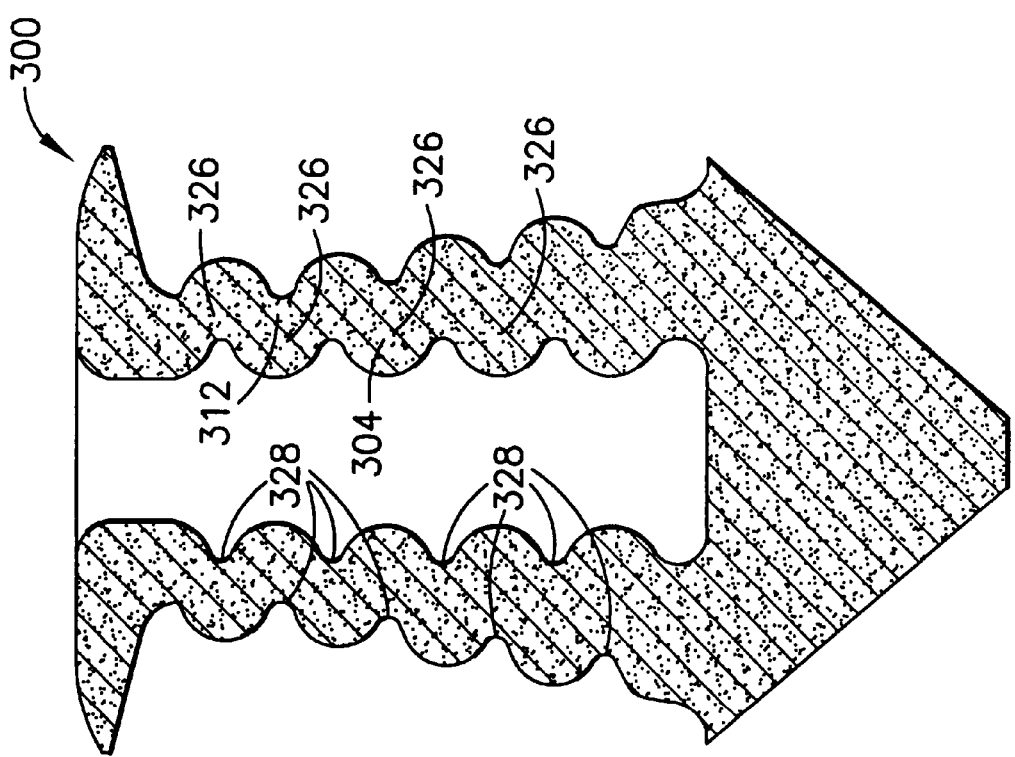
FIG. 9 is a section view of a punctum plug according to a third embodiment of the invention.

Referring now to FIG. 9, a third embodiment of the punctum plug 300 of the invention, substantially similar to the first embodiment (with like parts having numbers incremented by 200), is shown. The wall 312 of the shaft 304 of the plug includes undulations 326 and consequently folds 328 substantially along its entire length.

Figure 10:
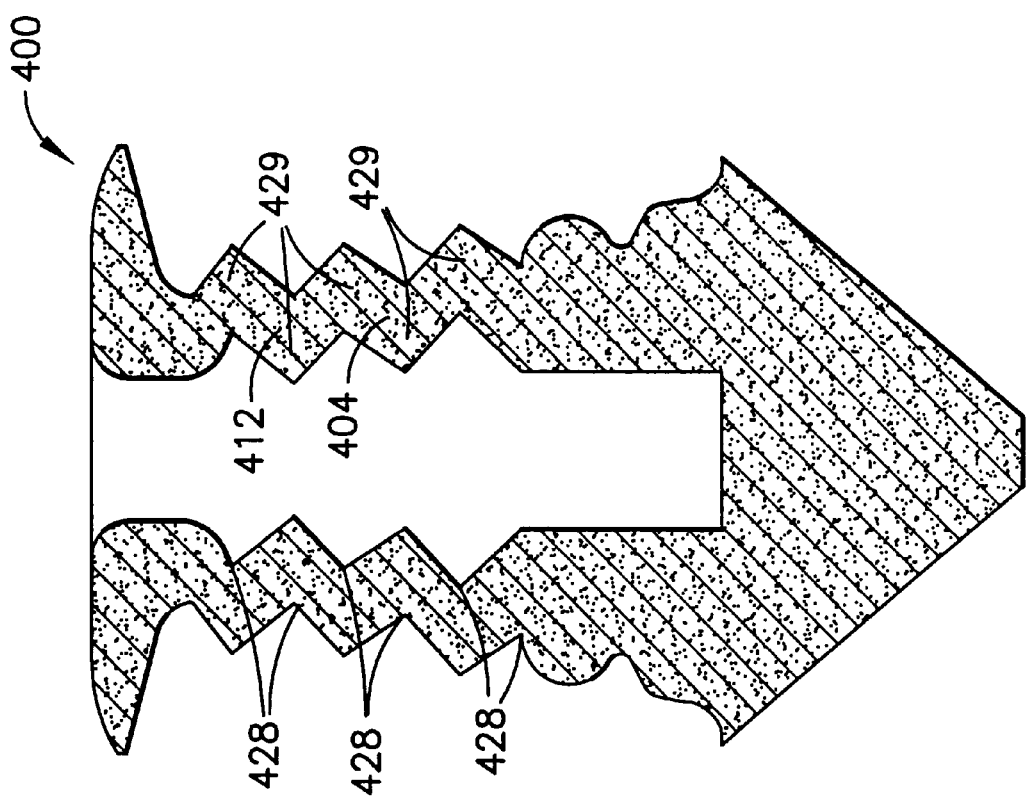
FIG. 10 is a section view of a punctum plug according to a fourth embodiment of the invention.

Turning now to FIG. 10, a fourth embodiment of the punctum plug 400 of the invention, substantially similar to the first embodiment (with like parts having numbers incremented by 300), is shown. The wall 412 of the shaft 404 of the plug includes relatively "sharp" undulations, which form substantially angular or accordion-like folds 428, each of which substantially comes to a point. The folds 428 are provided at least along a portion of the wall 412.

Figure 12:
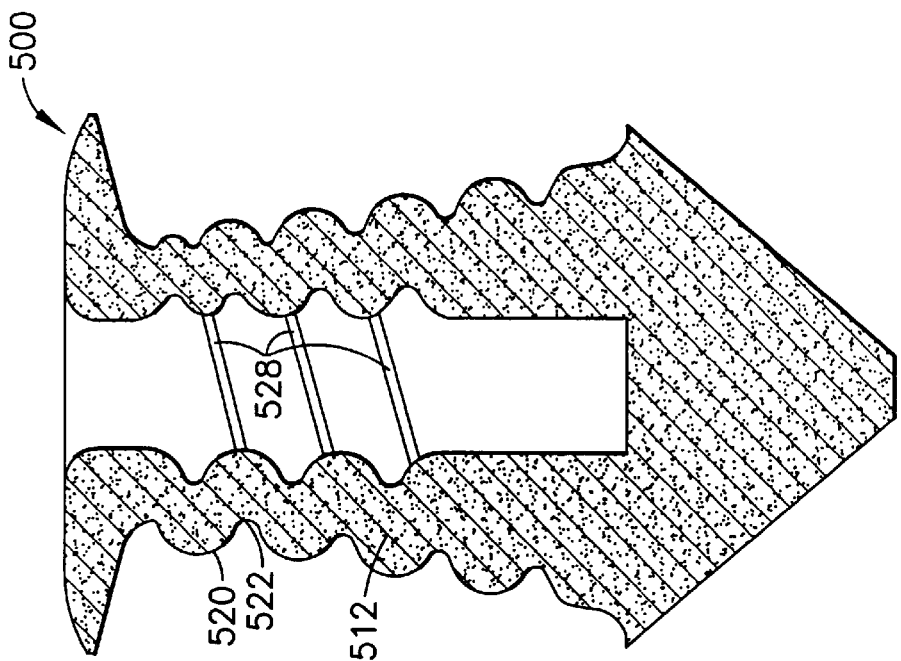
FIG. 12 is a section view through line 12—12 in FIG. 11.
Figure 11:
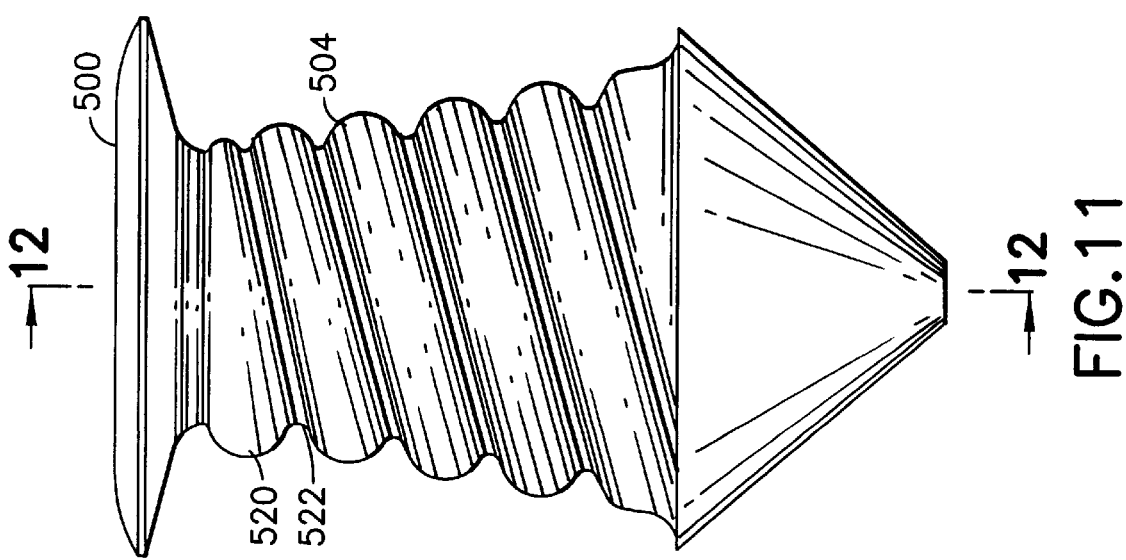
FIG. 11 is a side elevation view of a punctum plug according to a fifth embodiment of the invention.

Referring now to FIGS. 11 and 12, a fifth embodiment of the punctum plug 500 of the invention, substantially similar to the first embodiment (with like parts having numbers incremented by 400), is shown. The wall 512 of the shaft 504 of the plug is provided with a substantially helical convex ring 520 and a substantially helical concave ring 522, which together form a helical fold 528 about the shaft. The shaft may expand and compress about the fold 528.

Figure 13:
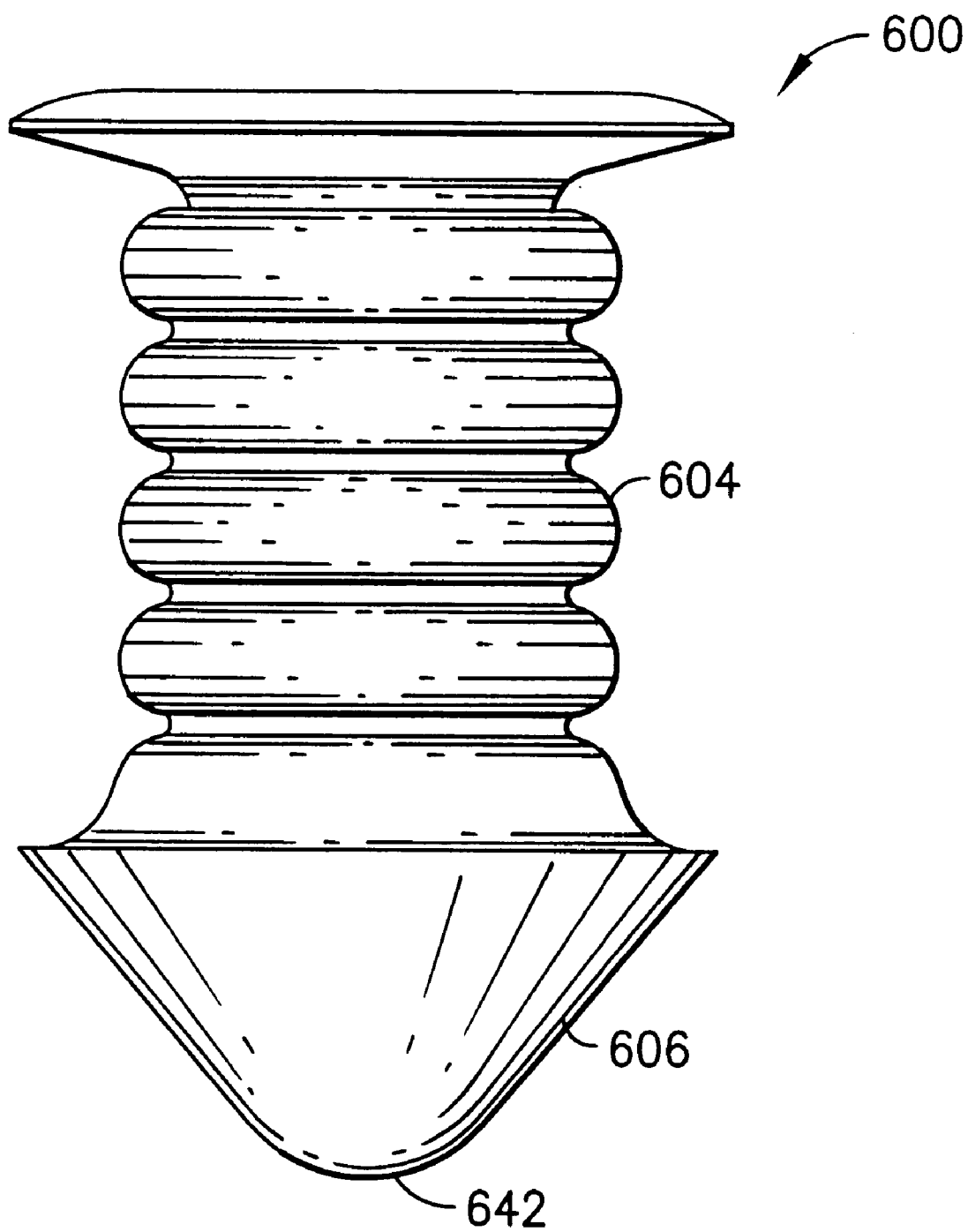
FIG. 13 is a side elevation of a punctum plug according to a sixth embodiment of the invention.

Turning now to FIG. 13, a sixth embodiment of the punctum plug 600 of the invention, substantially similar to the first embodiment (with like parts having numbers incremented by 500), is shown. The shaft 604 is substantially cylindrical; i.e., no substantial taper is provided along its length. In addition, the body 606 of the plug 600 has a substantially rounded tip 642.

Figure 15:
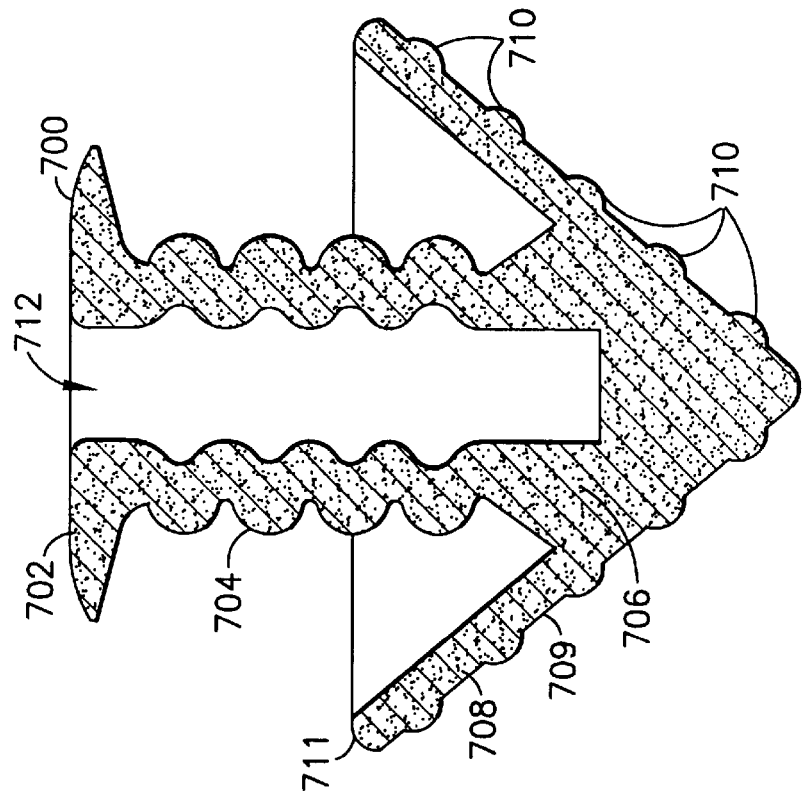
FIG. 15 is a section view across line 15—15 in FIG. 14.
Figure 14:
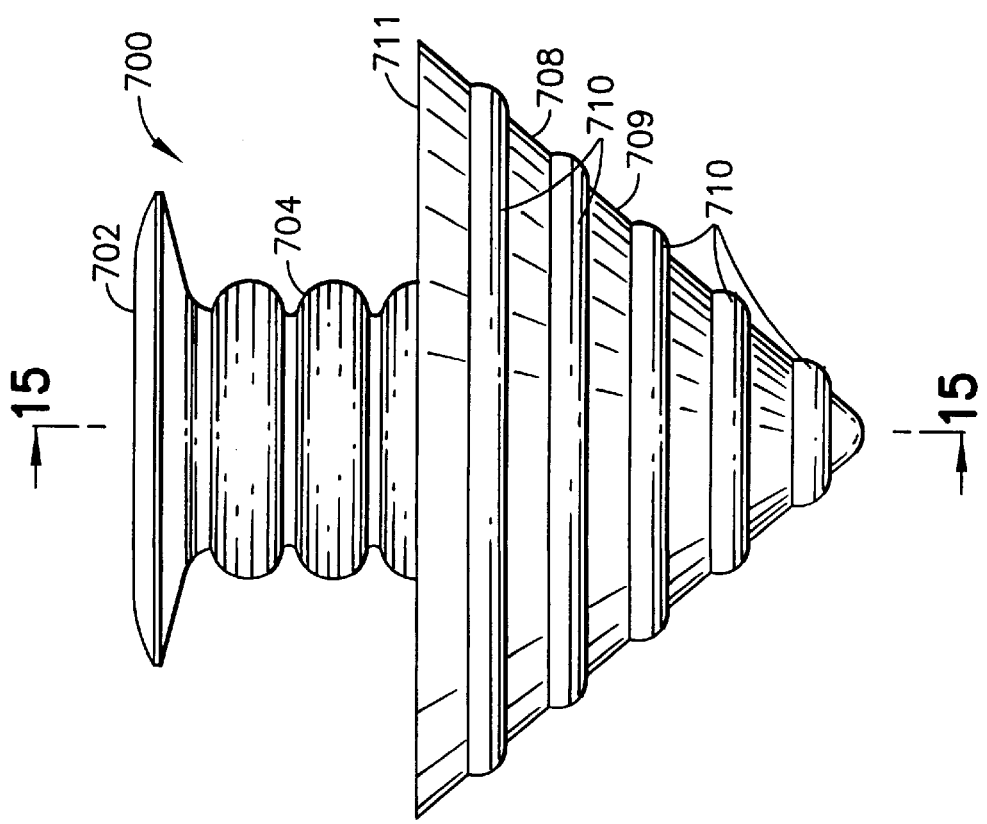
FIG. 14 is a side elevation of a punctum plug according to a seventh embodiment of the invention in a prior-to-implantation configuration.

Referring now to FIGS. 14 and 15, a seventh embodiment of the punctum plug 700 of the invention is shown. The plug 700 includes a head 702, a preferably collapsible and expandable shaft 704 (as described above), and a body 706. The shaft 704 is preferably non-tapered. The body 706 is provided with a preferably conical skirt portion 708. The skirt portion 708 defines a rim 711 which opens toward the head 702. The body 706, including the skirt portion 708, includes an exterior surface 709 which is provided with a plurality of circumferential traction ribs 710 which enhance traction between the plug 700 and the walls of the duct into which the plug is adapted to be inserted. Alternatively, other traction devices may be provided to the body 706; for example, wave-like or zig-zag ribs or a plurality of nubs. The head 702, shaft 704, and preferably a portion of the body 706 are provided with a bore 712.

Figure 17:
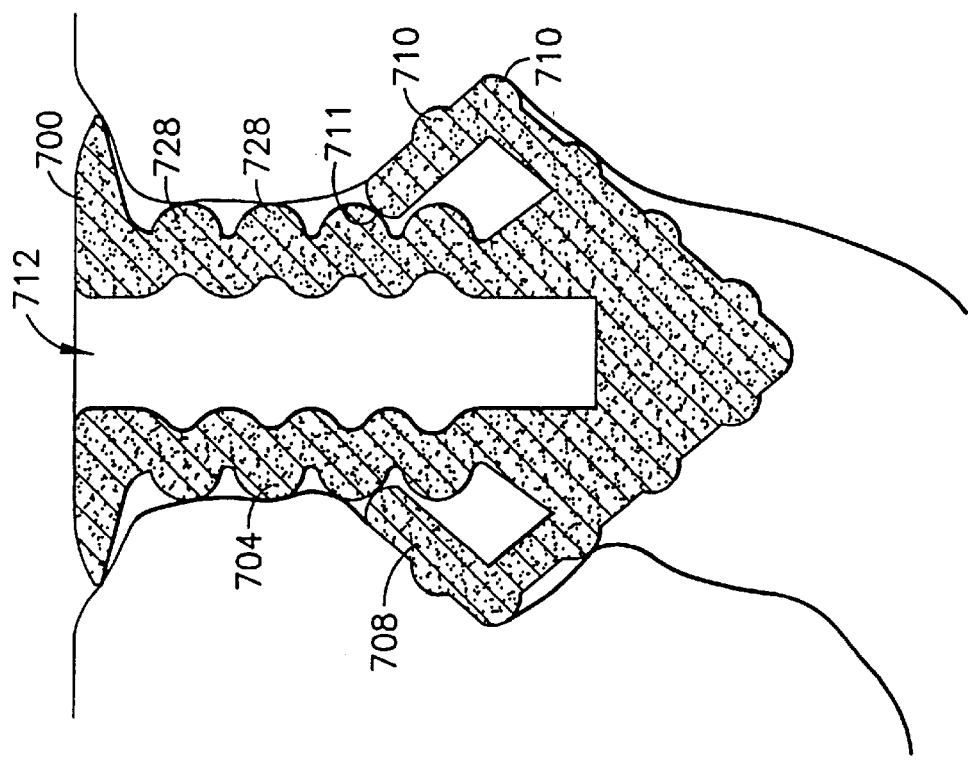
FIG. 17 is a section view across line 17—17 in FIG. 16.
Figure 16:
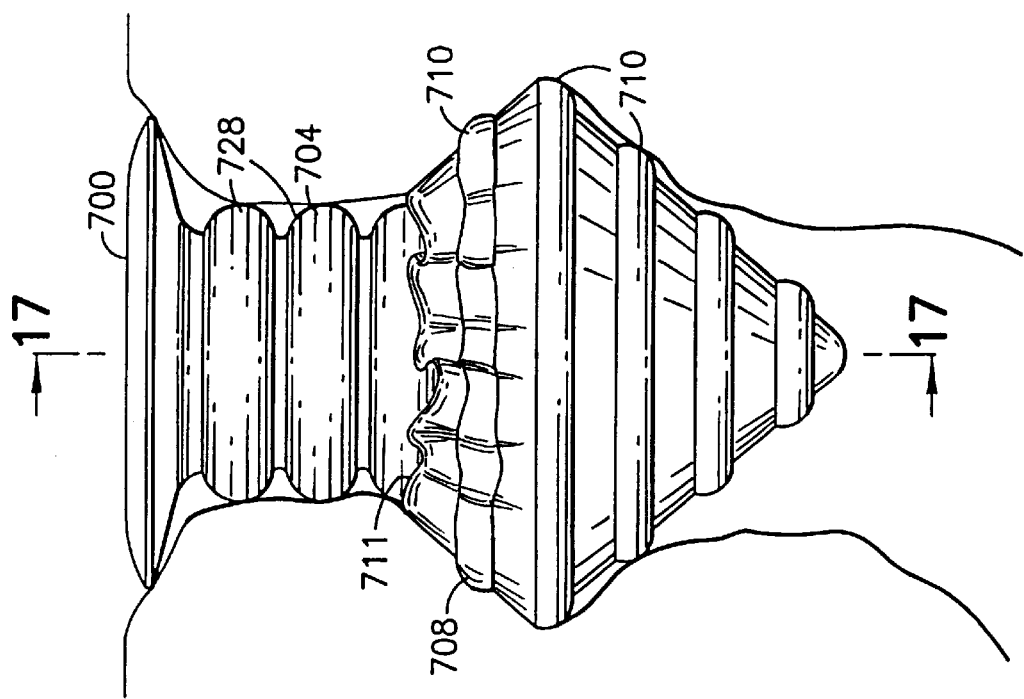
FIG. 16 is a side elevation of a punctum plug according to the seventh embodiment of the invention shown implanted in the punctum.

Turning now to FIGS. 16 and 17, the seventh embodiment of the punctum plug 700 is illustrated implanted in the punctal opening. The rim 711 of the skirt portion 708 collapses, or folds back, toward the shaft 704 to comfortably and securely seat the punctum plug within the punctum. In addition, the traction ribs 710 provide point contact against the duct walls of the punctum to enhance traction of the plug and further aid in the secure seating of the plug. Moreover, the curving exterior contours 728 of the shaft 704 provides additional traction locations. Also, as in the other embodiments, the shaft 704 preferably can adapt in length to provide the optimum anatomical fit within the punctum.

There have been described and illustrated herein several embodiments of a punctum plug for occluding the nasal lacrimal duct. While particular embodiments of the invention have been described, it is not intended that the invention be limited thereto, as it is intended that the invention be as broad in scope as the art will allow and that the specification be read likewise. Thus, while a lower profile head as described in co-owned and co-pending U.S. Ser. No. 09/095, 194 is preferred, it will be appreciated that other head designs may likewise be used with the plug of the invention. Also, while a particular body shape has been described, it will be appreciated that other body shapes may alternatively be used. In addition, while the first portion of the wall of the plugs is preferably the upper portion and the second portion is preferably the lower portion, it will be appreciated that the features described as comprising the first portion may alternatively be provided in the lower portion and the features described as comprising the second portion may be provided in the upper portion of the wall. Furthermore, it is intended that teachings in the several embodiments may be combined to provide other embodiments which are also considered to be the invention. In addition, while the plug has been described as preferably being made from silicone, it will be appreciated that other suitable materials known to those skilled in the art may also be used. Furthermore, different parts of the plug can be made from different materials. Moreover, while the methods of liquid injection molding, cast molding, and transfer molding are disclosed for making the plugs, other methods known in the art can also be used. It will therefore be appreciated by those skilled in the art that yet other modifications could be made to the provided invention without deviating from its spirit and scope as so claimed.

We claim:

1. A punctum plug for insertion into a punctal opening of a nasal lacrimal duct, said punctum plug comprising:
   a) a proximal head portion;
   b) a distal body portion sized to fit into the punctal opening; and
   c) a central shaft portion having a circumference and at least one fold substantially around said circumference, said shaft being able to at least one of flex and change in length due to said at least one fold,
      said head and said shaft at least partially defining a bore.

2. A punctum plug according to claim 1, wherein:
   said shaft portion is able to both flex and change in length due to said at least one fold.

3. A punctum plug according to claim 1, wherein:
   said shaft portion includes an upper portion provided with said at least one fold and a lower portion which defines a cylindrical portion of said bore.

4. A punctum plug according to claim 1, wherein:
   said shaft portion includes at least one convex portion and at least one concave portion which together define said at least one fold.

5. A punctum plug according to claim 4, wherein:
   said shaft portion includes a plurality of convex portions and a plurality of concave portions alternating displaced about a length of said shaft.

6. A punctum plug according to claim 1, wherein:
   said shaft portion is provided with a wall and said at least one fold is at least one angular undulation of said wall.

7. A punctum plug according to claim 1, wherein:
   said shaft portion tapers in a smaller diameter in the direction of said body portion to said head portion.

8. A punctum plug according to claim 1, wherein:
   said shaft portion includes a wall having a substantially constant thickness at and adjacent said at least one fold.

9. A punctum plug according to claim 1, further comprising:
   d) a flared skirt portion defining a rim which is collapsible toward said shaft.

10. A punctum plug according to claim 1, wherein:
    said body portion includes a conical skirt portion, and said body portion includes an exterior surface provided with traction means.

11. A punctum plug for insertion into a punctal opening of a nasal lacrimal duct, said punctum plug comprising:
    a) a proximal head portion;
    b) a distal body portion sized to fit within the punctal opening; and
    c) a shaft having an inner wall and an outer wall which are each provided with at least one undulation along a length of the shaft.

12. A punctum plug according to claim 11, wherein:
    said at least one undulation is smooth.

13. A punctum plug according to claim 11, wherein:
    said at least one undulation is angular.

14. A punctum plug according to claim 11, wherein:
    said shaft portion tapers to a smaller diameter in the direction of said body portion to said head portion.

15. A punctum plug according to claim 11, wherein:
    said at least one undulation defines a helical fold in said shaft.

16. A punctum plug according to claim 11, further comprising:
    d) a flared skirt portion defining a rim which is collapsible toward said shaft.

17. A punctum plug according to claim 11, wherein:
    said body portion discrete from said shaft portion includes a conical skirt portion discrete from said shaft portion, and said body portion includes an exterior surface provided with traction means.

18. A punctum plug for insertion into a punctal opening of a nasal lacrimal duct, said punctum plug comprising:
    a) a proximal head portion;
    b) a distal body portion sized to fit within the punctal opening; and
    c) a shaft having a wall which is provided with a plurality of curving portions along a length of the shaft.

19. A punctum plug according to claim 18, wherein:
    a least some of said plurality of curving portions are convex.

20. A punctum plug according to claim 19, wherein:
    said shaft portion is provided with a fold substantially around said circumference of said shaft between each of said convex curving portions.

21. A punctum plug according to claim 18, wherein:
    at least some of said plurality of curving portions are concave.

22. A punctum plug according to claim 21, wherein:
    said shaft is provided with an apex portion between each of said convex curving portions.

23. A punctum plug according to claim 18, wherein:
    A plurality of curving portions are convex and said shaft further includes along said length of said shaft at least one circumferential concave curving portion.

24. A punctum plug according to claim 18, wherein:
    said shaft portion tapers to a smaller diameter in a direction of said body portion to said head portion.

25. A punctum plug according to claim 18, further comprising:

d) a flared skirt portion defining a rim which is collapsible toward said shaft.

26. A punctum plug according to claim 18, wherein:

said body portion includes a conical skirt portion, and said body portion includes an exterior surface provided with traction means.

27. A punctum plug for insertion into a punctal opening of a nasal lacrimal duct, said punctum plug comprising:

a) a proximal head portion;

b) a distal body portion sized to fit within the punctal opening; and c) a shaft having a wall which has a length over which said wall changes in thickness at a nonconstant rate.

* * * * *